United States Patent [19]
Guri

[11] Patent Number: 5,803,014
[45] Date of Patent: Sep. 8, 1998

[54] HABITAT MEDIA FOR ANTS AND OTHER INVERTEBRATES

[75] Inventor: Assaf Guri, Cherry Hill, N.J.

[73] Assignee: Plant Cell Technology, Inc., Washington, D.C.

[21] Appl. No.: 880,003

[22] Filed: Jun. 20, 1997

Related U.S. Application Data

[60] Provisional application No. 60/040,315 Feb. 14, 1997.

[51] Int. Cl.[6] .................................................. A01K 67/00
[52] U.S. Cl. .............................................................. 119/6.5
[58] Field of Search .............................. 119/6.5, 6.6, 6.7, 119/6.8

[56] References Cited

U.S. PATENT DOCUMENTS

| | | | |
|---|---|---|---|
| 2,527,214 | 10/1950 | Graves | 119/6.7 |
| 4,417,545 | 11/1983 | Finney | 119/6.7 |
| 4,840,800 | 6/1989 | Harris | 119/6.5 |

FOREIGN PATENT DOCUMENTS

| | | | |
|---|---|---|---|
| WO/96/38542 | 12/1996 | European Pat. Off. | |
| 6276892 | 10/1994 | Japan | 119/6.5 |
| 1629009 | 2/1991 | U.S.S.R. | 119/6.5 |

*Primary Examiner*—Thomas Price
*Attorney, Agent, or Firm*—Schweitzer Cornman Gross & Bondell LLP

[57] ABSTRACT

A soil-less habitat medium, especially for ants, allows the sustained viability of an ant or ant colony without the provision of additional nutrients. The medium comprises the combination of a culture medium and a chemical agent to reduce or prevent microbial contamination of the culture medium. The medium is preferably in the form of a clear or tinted gel, and allows the ants to be observed throughout the medium. The medium is of particular value for use in an ant vivaria.

16 Claims, No Drawings

HABITAT MEDIA FOR ANTS AND OTHER INVERTEBRATES

This application claims the benefit of U.S. Provisional application Ser. No. 60/040,315, filed Feb. 14, 1997.

FIELD OF THE INVENTION

The present invention relates to colloidal and solid media for animal habitats, particularly invertebrates, and most particularly ants. The disclosed compositions can be used to create artificial habitats for invertebrates which are clean, clear or any selected color, and have the necessary nutrients for invertebrates to sustain life.

BACKGROUND OF THE INVENTION

In nature, the soil provides a habitat for a diverse group of animal life. In addition to providing shelter, the soil may serve as a carrier and a repository for moisture as well as other minerals and nutrients required by the organisms living therein.

The growth and culture of animals, and particularly invertebrates, in a closed and contained structure is well known. Ants, in particular, have long been the subject of such artificial habitats, or "ant farms," in which a structure having one or more clear sides is filled with soil. A colony of ants inhabits the soil, and may be observed to some degree through the clear enclosure walls.

In order to maintain such an environment, it is frequently necessary to provide water and nutrients for the ant colony. Some nutrients may be provided by allowing plants to grow in the habitat. As a general rule, however, the continuous replenishment of water and nutrients is required to maintain a viable habitat. In addition, such a closed environment often provides a fertile breeding ground for a variety of unwanted micro-organisms. Mold, fungi and bacteria can thrive, and often provide a untimely demise to the ant population.

In addition to the foregoing, artificial soil habitats have a general limitation that the container for the soil must be constructed with a relatively narrow depth to maximize the portion of the underground colony formed which can be observed through a side wall. The darkness and general nature of the soil impairs or prevents observation of ant activities more than a couple millimeters away from the side walls.

The use of colloidal and solid artificial growth media are known and used for plants, bacteria, and other microbials. Such plant cultures typically consist of water, mineral salts, and other ingredients such as phytohormones, vitamins, one or more carbon sources, such as sucrose or glucose, and one or more growth enhancers. Conventional culture media must be maintained in a sterile environment to prevent contamination by bacteria and other unwanted organisms. The use of such media has generally been considered as unsuitable for use as a habitat for complete organisms such as ants or other invertebrates. Beyond the apparent differences between soil and such media, the requirement for continued sterility, and the ability of such media to support bacterial and fungal growth teach away from the use of of such media for an ant habitat.

It is an objective of the present invention to provide a composition which may be used in lieu of soil as a habitat media for invertebrates and, in particular for ants.

A further objective of the present invention is to provide a habitat for the continued sustenance of ant life and which may further provide a source of nutrients for the ants.

A further objective of the present invention is to provide a composition and method for maintaining an artificial soil environment for ants in which microbial contamination is reduced or prevented throughout the useful life of the media.

A further object of the present invention is to provide a soil-less habitat and nutritional media for normally soil-living animals, such as ants, which allows for the increased observation of such animals throughout the media.

BRIEF SUMMARY OF THE INVENTION

Published PCT application WO 96/38542 of the present inventor and another discloses compositions and methods for the prevention of microbial contamination of plant tissue culture media. In particular, such compositions and methods prevent or inhibit microbial growth in culture media for plant tissue cultures which normally require maintenance of sterile conditions. Specific chemical agents are used in the culture medium at concentrations that reduce or prevent microbial contamination but which allow for substantially normal germination of seeds or substantially normal growth of development of plants, plant organs, plant tissues or plant cells.

The present invention is directed to a soil-less animal habitat medium comprising a cell or tissue culture medium incorporating a chemical agent at a concentration that effectively reduces or prevents the growth of bacteria and fungi and that allows for substantially normal survival and sustenance of a complex animal organism, such as an ant or a colony of such organisms. The habitat medium is in the form of a solid, and preferably a gel, which may be clear or colored, and which allows observation of the animals throughout the media for which it provides a habitat. In a particular contemplated embodiment, the habitat media may serve as a habitat for an ant colony, which can thrive in the media for an extended length of time without the necessity for external nutrient replacement.

DETAILED DESCRIPTION OF THE INVENTION

The present invention provides compositions and methods to maintain a self-sustaining ant habitat or colony by providing a soil-less environment capable of providing both a habitat and moisture and nutrition source for ants over an extended period. A chemical agent is incorporated into a cell or tissue culture medium in a concentration that is effective to reduce or prevent the growth of bacteria and fungi and that allows for substantially normal and sustained survival and nurture of the ants.

The chemical agent useful in practicing the present invention preferably comprises a mixture of methylchloroisothazolinone (5-chloro-2-methyl-4-isothiazolin-3-one), methylisothiazolinone (2-methyl-4-isothiazolin-3-one), magnesium chloride and magnesium nitrate. More preferably, the chemical agent comprises a mixture of methylchloroisothiazolinone, methylisothiazolinone, magnesium chloride, magnesium nitrate, and potassium sorbate and sodium benzoate.

Applicant has surprisingly discovered that a combination of a solid cell or tissue culture media in combination with these combinations of chemicals, in a particular range of concentrations, are effective as an ant habitat and sustaining ant life without the introduction of other nutrients while reducing or preventing microbial contamination for an extended duration, thus helping to ensure the survival of the ant colony raised within the media. The ants utilize the medium as both a replacement for a soil matrix in which a colony can be maintained, and as a nutrition source, providing both food and water. Thus, no additional foodstuffs needs to be provided.

The relative concentrations of the individual components comprising the chemical agent may be varied to produce a mixture that is optimally effective in practicing the present invention for the ant colony. However, a preferred mixture of the components in the chemical agent comprises: methylchloroisothiazolinone in a concentration range of about 2.0 to about 2.6 g/l; methylisothiazolinone in a concentration range of about 0.6 to about 0.8 g/l; magnesium chloride in a concentration range of about 15.0 to 30 g/l.

A more preferred mixture of the components in the chemical agent further comprises: potassium sorbate in a concentration range of about 15 to about 25 g/l or sodium benzoate in a concentration range of about 13 to about 27 g/l.

In all cases, the components of the chemical agent are mixed to form a stock solution of chemical agent using any liquid in which the components will dissolve, but preferably in water, and most preferably in distilled or deionized water.

As used in the present application, "microbial contamination" refers to the growth of any unwanted microorganisms, e.g., bacteria or fungi, in a cell or tissue culture medium.

As used in the present application, "cell or tissue culture medium," "culture medium," and "medium" refer to a solid substrate (including gels), having nutrients and other materials used for the growth of micro-organisms and plant and animal tissues in culture, including but not limited to such substrates in which a plant seed will germinate, a plant can be maintained or grown, an isolated plant or animal organ or animal tissue can be maintained, propagated or differentiated, or one or more isolated plant cells, plant cell aggregates or plant cell protoplasts may be maintained, propagated or differentiated and which is to be maintained in a sterile condition, i.e., substantially free of microbial contamination.

The terms "cell or tissue culture medium," "culture medium," and "medium" are further intended to refer to solid media containing water and an appropriate mixture of mineral salts. The culture medium may further incorporate, in appropriate concentrations, phytohormones including, for example, auxins, cytokinins or gibberellins, vitamins, such as one or more B-vitamins, one or more carbon sources including, for example sucrose or glucose, and one or more undefined growth enhancers, such as coconut milk, as generally known in the art. For example, the mineral salts may be selected from any number of commercially available mixtures (e.g., from Sigma Chemical Co., St. Louis, Mo.). Mineral salt mixtures useful in the practice of the present invention include, for example, Hoagland's basal salt mixture, Gamborg's B-5 basal salt mixture, Heller's basal salt mixture, Murashige and Skoog basal salt mixture, and variations thereof. In addition, various macronutrients, micronutrients and vitamin components known in the art may be included in the culture media. Such a culture media may be, for example, Murashige and Skoog mineral salts and 2% (w/w) sucrose.

According to the method of the present invention, the chemical agent is added to the culture medium in a concentration that will reduce or prevent the growth of bacteria or fungi, or both, and that will allow substantially normal growth of an ant or ant colony utilizing the culture media as a habitat and as a nutrition source.

As used in the present invention, a chemical agent is effective at reducing or preventing microbial growth in a culture medium if addition of the chemical agent to the plant culture medium at the concentration that allows substantially normal growth or development of the ants, and reduces the amount of bacterial or fungal contamination by at least 80% compared to control media lacking the chemical agent. A preferred range of concentrations of the chemical agent in the culture medium is from about 0.02% to about 0.07% (v/v). A preferred chemical agent is the Kathon product of Rohn & Haas. An ultimate concentration of methylchloroisothiazolinone in a range of 2.3 to 8.01 mg/l of culture media, methylisothiazolinone in a range of 0.6 to 2.1 mg/l, with magnesium salts, preferably $Mg(NO_3)_2$ and $MgCl_2$ in a range of 46–161 mg/l has been found preferable for culture of harvester ants of a species generally known and used in ant vivaria, such as Pogononyrmex Occidentalis.

A gelling agent, for example, PHYTAGEL™ gellan gum (Sigma Chemical Co.), in an appropriate concentration range, for example, from 0.2% to 0.3% (w/v) for gellan gum, may be added to the culture medium. The culture medium must then be sufficiently heated, e.g., by autoclaving, to dissolve the gelling agent. The presence of the chemical agent, however, renders autoclaving for the purpose of sterilization unnecessary.

After autoclaving, culture medium comprising chemical agent and the dissolved gelling agent may then be transferred to individual habitat containers of any type appropriate for an ant habitat or vivarium and the medium allowed to cool and solidify.

An additional benefit of the chemical agent is that, where autoclaving is not needed to dissolve a gelling agent, heat-labile components of the culture medium such as vitamins and sugars will no longer require filter-sterilization. The culture medium so prepared may be stored for an extended period of time or used immediately.

The present invention further provides an ant habitat kit comprising a chemical agent in a concentration that is effective to reduce or prevent microbial contamination for an extended duration and that allows for substantially normal ant life over that duration which kit comprises a culture or habitat container comprising a cell or tissue culture medium comprising the chemical agent, as well as a quantity of ants to be raised in the culture container.

Having now generally described the invention, the same will be more readily understood through reference to the following examples which are provided by way of illustration, and are not intended to be limiting of the present invention.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A soil-less ant habitat medium providing both a habitat and nutrients comprising the combination of a culture medium and a chemical agent, which chemical agent comprises: methylchloroisothiazolinone in a concentration range of about 2.0 to 2.6 g/l; methylisothiazolinone in a concentration range of about 0.6 to about 0.8 g/l; magnesium chloride in a concentration range of about 15.0 to 30 g/l; and magnesium nitrate in a concentration range of about 15.0 to 30 g/l; wherein the chemical agent is present in the culture medium at a concentration that reduces or prevents microbial contamination of the culture medium and allows for the substantially sustained viability of the ants inhabiting the habitat media.

2. The ant habitat medium of claim 1, wherein the chemical agent further comprises potassium sorbate in a concentration range of about 15 to about 25 g/l.

3. The ant habitat medium of claim 1, wherein the chemical agent further comprises sodium benzoate in a concentration range of about 13 to about 27 g/l.

4. The ant habitat medium of claim 1, wherein the chemical agent further comprises potassium sorbate in a concentration range of about 15 to about 25 g/l and sodium benzoate in a concentration range of about 13 to about 27 g/l.

5. The ant habitat medium of claim 4, wherein the chemical agent is present in the culture medium in a concentration range of about 0.02% (v/v) to about 0.20% (v/v).

6. The ant habitat medium of claim 1 or claim 4, wherein said culture medium is a plant culture medium.

7. The ant habitat medium of claim 6, wherein said culture medium comprises Murashige and Skoog mineral salts.

8. The ant habitat medium of claim 7, wherein said culture medium includes sucrose in a concentration of about 2% w/w.

9. An ant vivarium kit comprising:

(a) a vivarium container;

(b) ants; and (c) the ant habitat medium of claim 1.

10. The ant vivarium kit of claim 9, wherein the chemical agent further comprises potassium sorbate in a concentration range of about 15 to about 25 g/l.

11. The ant vivarium kit of claim 9, wherein the chemical agent further comprises sodium benzoate in a concentration range of about 13 to about 27 g/l.

12. The ant vivarium of claim 9, wherein the chemical agent further comprises potassium sorbate in a concentration range of about 15 to about 25 g/l and sodium benzoate in a concentration range of about 13 to about 27 g/l.

13. The ant vivarium kit of claim 12, wherein the chemical agent is present in the culture medium in a concentration range of about 0.02 (v/v) to about 0.20% (v/v).

14. The ant vivarium kit of claim 9 or claim 12, wherein said culture medium is a plant culture medium.

15. The ant vivarium kit of claim 14, wherein said culture medium comprises Murashige and Skoog mineral salts.

16. The ant vivarium kit of claim 15, wherein said culture medium includes sucrose in a concentration of about 2% w/w.

* * * * *